United States Patent
Msika et al.

(10) Patent No.: US 7,763,647 B2
(45) Date of Patent: Jul. 27, 2010

(54) TOPICAL SOLUTION CONTAINING A CHROMANE OR CHROMENE DERIVATIVE

(75) Inventors: Philippe Msika, Versailles (FR); Antoine Piccirilli, Versailles (FR); Nathalie Piccardi, St. Egreve (FR); Nicole Broutin, Alluyes (FR)

(73) Assignee: Laboratories Expanscience, Courbevoie (FR)

( * ) Notice: Subject to any disclaimer, the term of this patent is extended or adjusted under 35 U.S.C. 154(b) by 847 days.

(21) Appl. No.: 10/468,769

(22) PCT Filed: Feb. 21, 2002

(86) PCT No.: PCT/FR02/00650

§ 371 (c)(1),
(2), (4) Date: Oct. 16, 2003

(87) PCT Pub. No.: WO02/066001

PCT Pub. Date: Aug. 29, 2002

(65) Prior Publication Data

US 2004/0067246 A1  Apr. 8, 2004

(30) Foreign Application Priority Data

Feb. 21, 2001 (FR) .................................. 01 02319

(51) Int. Cl.
*A01N 43/16* (2006.01)
(52) U.S. Cl. ...................... 514/451; 514/456
(58) Field of Classification Search ................... 514/451
See application file for complete search history.

(56) References Cited

U.S. PATENT DOCUMENTS

| | | | | |
|---|---|---|---|---|
| 4,556,560 A * | 12/1985 | Buckingham | ................ | 424/641 |
| 5,013,853 A * | 5/1991 | Gericke et al. | .............. | 549/401 |
| 5,824,702 A * | 10/1998 | Wei | ............................. | 514/456 |
| 6,004,558 A | 12/1999 | Thurn et al. | | |
| 6,019,992 A | 2/2000 | Carson et al. | | |
| 6,060,070 A | 5/2000 | Gorbach | | |
| 6,180,662 B1 | 1/2001 | Lanzendorfer et al. | | |
| 2004/0238781 A1* | 12/2004 | Landauer et al. | ............... | 252/1 |

OTHER PUBLICATIONS

The Merck Index An Encyclopedia of Chemicals and Drugs, 1976, 9th Edition, p. 4224.*

* cited by examiner

*Primary Examiner*—Sreeni Padmanabhan
*Assistant Examiner*—Layla Soroush
(74) *Attorney, Agent, or Firm*—Foley & Lardner LLP

(57) ABSTRACT

The invention relates to compositions intended for external topical use comprising a true solution containing a chromane or chromene derivative having formula (I), preferably a flavonoid, dissolved in a suitable solvent. The invention also relates to a method for preparing such compositions and the use of said compositions as sun protection agents for the skin, advantageously as agents having an anti-erythemal, anti-oxidant, anti-radical, anti-inflammatory or vasculotropic activity.

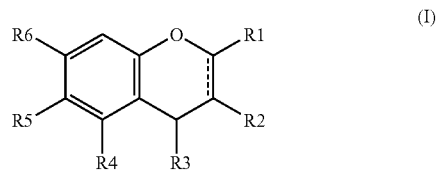

13 Claims, No Drawings

TOPICAL SOLUTION CONTAINING A CHROMANE OR CHROMENE DERIVATIVE

The present invention relates to compositions intended for external topical use comprising a true solution containing a chroman or chromene derivative, advantageously a flavonoid, dissolved in an appropriate solvent. The subject of the invention is also a method for preparing such compositions and the use of these compositions as sun protection agents for the skin, advantageously as agents having an antierythemal, antioxidant, anti-free-radical, anti-inflammatory or vasculotropic activity.

Compounds of the flavonoid type, such as flavones, flavanones, flavonols, aurones and chalcones, which are natural or synthetic, are potent antioxidants and often exhibit high inhibitory activities for enzymes in general. These properties explain the use of these active molecules in the cosmetic, pharmaceutical and nutritional fields.

In particular, genistein is known as a preventive agent against skin problems and skin cancers induced by UV rays (WO 97/46208). Genistein may thus be administered by the topical route in order to prevent and treat skin inflammations and irritations such as erythemas.

The applicant has discovered, surprisingly, that the sun protection activities, in particular the anti-erythemal, antioxidant, anti-free-radical, anti-inflammatory and vasculotropic activities, of a compound such as genistein increase significantly when said compound is solubilized beforehand in an appropriate solvent, such as polyethylene glycols, polypropylene glycols, derivatives thereof, ethoxylated fatty alcohols and polyols, and mixtures thereof.

Polyethylene glycol is a known solvent for soybean isoflavones. Dietary formulations in the form of micro/nanoemulsions containing micelles of very low diameter may thus be obtained by mixing an isoflavonoid with polyethylene glycol 400 (WO 99/38509). However, given that micro/nanoemulsions are not homogeneous, the quantity of active ingredient contained in this type of emulsions is difficult to determine and the preparation of compositions containing these micro/nanoemulsions is difficult to carry out.

However, it has been discovered, surprisingly according to the invention, that it was possible to use polyethylene glycol in combination with a compound such as genistein in order to form a true solution, free of the disadvantages described above, in a cosmetic composition or in a medicament suitable for use by the external topical route and intended to act as a (surface and cellular) sun protection agent for the skin, and more particularly as an antierythemal, antioxidant, anti-free-radical, anti-inflammatory or vasculotropic agent.

Furthermore, polyethylene glycols, polypropylene glycols, esters thereof and ethoxylated fatty alcohols and polyols have been found to be cosmetically acceptable compounds which are not aggressive for the skin, which are nontoxic, which are hypoallergenic and which offer the advantage, for the formulator, of facilitating the formation of stable emulsions while providing, through their solvent power, the solubility of the active ingredients of the composition.

Thus, the solubilization of a compound such as a flavonoid prior to its incorporation into a cosmetic or pharmaceutical composition not only gives the advantage of increasing the penetration and the bioavailability of said compound in order to potentiate and enhance its biological activities, such as its sun protection activity for the skin, but also of facilitating the preparation and the use of such a composition.

The subject of the present invention is thus compositions intended for an external topical use comprising at least one true solution containing at least one compound (a) dissolved in a solvent (b), said solvent (b) being chosen from the group consisting of polyethylene glycols, polypropylene glycols, derivatives thereof, ethoxylated fatty alcohols and polyols, and mixtures thereof, and said compound (a) being a chroman or chromene derivative corresponding to general formula (I)

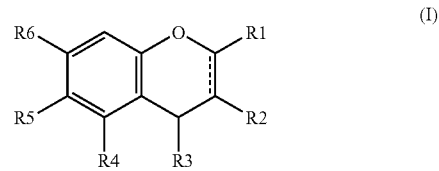

in which:

the dotted line represents an additional bond or the absence of an additional bond;

$R_1$ represents a hydrogen atom, a hydroxyl radical, a methoxy radical, a phenyl radical, a phenyl radical substituted with 1, 2 or 3 hydroxyl groups, a phenyl radical substituted with 1, 2 or 3 methoxy groups or a phenyl radical substituted with a flavone radical of formula:

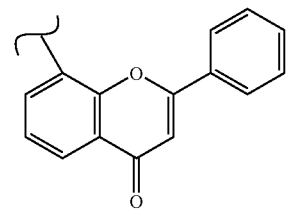

$R_2$ represents a hydrogen atom, a hydroxyl radical, a methoxy radical, a phenyl radical, a phenyl radical substituted with 1, 2 or 3 hydroxyl groups or a phenyl radical substituted with 1, 2 or 3 methoxy groups or alternatively $R_1$ and $R_2$ form together a benzene ring;

$R_3$ represents a hydrogen atom, a hydroxyl radical or an oxo radical;

$R_4$, $R_5$ and $R_6$, which are identical or different, represent a hydrogen atom, a hydroxyl radical, a methoxy radical, a phenyl radical, a phenyl radical substituted with 1, 2 or 3 hydroxyl groups or a phenyl radical substituted with 1, 2 or 3 methoxy groups.

The term "true solution" is understood to mean, for the purposes of the present invention, any clear or limpid homogeneous solution which is not a micro- or a nano-emulsion, which does not contain micelles and whose active ingredient concentration remains appreciable and precisely quantifiable by chromatographic assay.

In one particular embodiment of the present invention, the compound (a) is chosen from the group consisting of chromones, xanthones and flavonoids. According to the present invention, the compound (a) is advantageously a flavonoid.

The term "flavonoid" is understood to mean, for the purposes of the present invention, compounds comprising two aromatic rings linked to each other by three carbon atoms, which together form an oxygenated heterocycle. Advantageously, according to the present invention, the flavonoid is chosen from the group consisting of flavones, flavonols, 2,3-dihydroflavonols, flavanones, flavanols, flavandiols, isoflavonoids and biflavonoids.

The term "flavanol" is understood to mean, for the purposes of the present invention, 3-hydroxyflavans or 4-hydroxyflavans. The term "flavan" is understood to mean, for the purposes of the present invention, the compounds of formula:

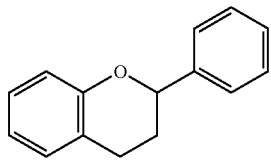

The term "flavandiol" is understood to mean, for the purposes of the present invention, 3,4-dihydroxy-flavans.

The term "isoflavonoid" is understood to mean, for the purposes of the present invention, the isoflavones and the isoflavans having the structural formula 3-phenyl-4-oxo-2,3-dihydrochromenes.

The term "biflavonoid" is understood to mean, for the purposes of the present invention, the compounds of formula:

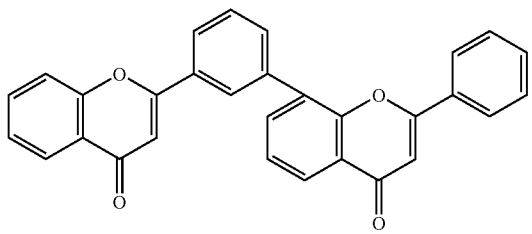

According to the present invention, the flavonoid is advantageously an isoflavone or a mixture of isoflavones. The isoflavones which can be used according to the present invention are obtained by chemical synthesis or are natural substances extracted from natural products, in particular from plants. The aglycone forms of the isoflavones and the glycosylated forms of the latter can be distinguished. These various forms are illustrated by the following formulae.

Aglycone forms, of formula:

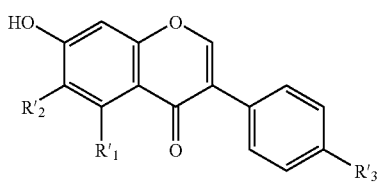

in which $R'_1$ represents a hydrogen atom or a hydroxyl group, $R'_2$ represents a hydrogen atom or a methoxy group and $R'_3$ represents a hydroxyl group.

Advantageously, according to the present invention, $R'_1$, $R'_2$ and $R'_3$ represent:

| $R'_1$ | $R'_2$ | $R'_3$ | Name of the compound |
|---|---|---|---|
| H | H | OH | Daidzein |
| OH | H | OH | Genistein |
| H | OCH$_3$ | OH | Glycitein |

Glycosylated forms, of formula:

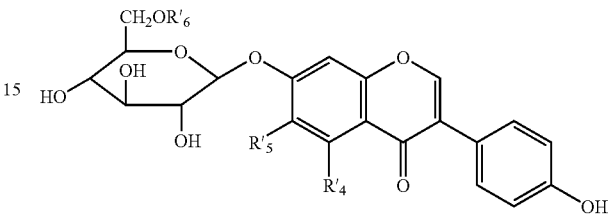

in which $R'_4$ represents a hydrogen atom or a hydroxyl group, $R'_5$ represents a hydrogen atom or a methoxy group and $R'_6$ represents a hydrogen atom.

Advantageously, according to the present invention, $R'_4$, $R'_5$ and $R'_6$ represent:

| $R'_4$ | $R'_5$ | $R'_6$ | Name of the compound |
|---|---|---|---|
| H | H | OH | Daidzein |
| OH | H | OH | Genistein |
| H | OCH$_3$ | OH | Glycitein |

The glycosylated forms of the isoflavones are the most abundant in nature. However, the aglycone isoflavones exhibit biological activities which are markedly higher than their glycosylated homologs. Such is the case for natural isoflavones such as genistein (1), daidzein or glycitein.

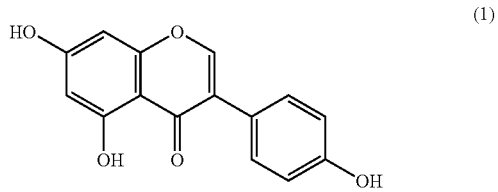

(1)

According to the present invention, the isoflavone is advantageously an aglycone isoflavone, preferably chosen from the group consisting of genistein, daidzein and glycitein. Still more advantageously, the flavonoid (a) is genistein. In particular, the genistein which can be used according to the present invention is a product of plant origin, having the titer 85 to 90% by weight.

In another particular embodiment of the present invention, the solvent (b) is chosen from the group consisting of polyethylene glycols and polypropylene glycols, advantageously having low molecular weights. The term polyethylene glycols and polypropylene glycols "having low molecular weights" is understood to mean, for the purposes of the present invention, polyethylene glycols and polypropylene glycols having an average molecular weight of less than or equal to 600, advantageously of between 200 and 600. Still more advantageously, the solvent (b) is polyethylene glycol 300 (PEG300).

Still more advantageously, the compound (a) is present at a concentration of between 0.1 and 1.2% by weight relative to the total weight of the composition intended for external topical use, and in particular the compound (a) is present at a concentration of between 0.1 and 12% by weight relative to the total weight of the true solution as defined above, consisting of the compound (a) dissolved in the solvent (b). Advantageously, the solvent (b) is present at a concentration of between 0.5 and 15% by weight relative to the total weight of the composition intended for external topical use.

The compositions according to the present invention may moreover contain cosmetically or pharmaceutically acceptable excipients, and conventional cosmetic additives, in particular organic or inorganic UVB/UVA screening agents, antioxidants, anti-free-radical agents, irradiated cellular protectants, anti-aging active agents known to persons skilled in the art (retinoids, vitamins, avocadofurans, unsaponifiable components, and the like).

The compositions according to the present invention may be provided in particular in the form of a single-phase or multiphase aqueous or aqueous-alcoholic lotion, a single-phase or multiphase gel, an emulsion, a cream, a vesicular dispersion, a mousse or a spray.

The subject of the present invention is also a method for preparing these compositions, characterized in that it comprises the step of solubilizing the compound (a) in the solvent (b), at room temperature, with stirring, for a period of between 10 and 120 minutes, advantageously for 30 minutes.

The subject of the present invention is also the cosmetic use of the compositions described above as sun protection agents for the skin, in particular as anti-oxidants, as anti-free-radical agents, as anti-inflammatory agents or as vasculotropic agents.

The subject of the present invention is also the use of the compositions described above for the preparation of a medicament intended to act as a sun protection agent for the skin, in particular as an antioxidant, as an anti-free-radical agent, as an anti-inflammatory agent or as a vasculotropic agent.

The subject of the present invention is also the use of the compositions described above for the preparation of a cosmetic product intended to prevent and/or reduce erythemas, in particular actinic erythemas induced by UVA and/or UVB radiation.

Advantageously, the compositions of the present invention are applied directly to the skin before and/or during and/or after exposure to sunlight, advantageously after the appearance of an erythema on the skin.

The subject of the present invention is also the use of the compositions described above for the preparation of a medicament capable of reducing and/or preventing erythemas, in particular actinic erythemas induced by UVA and/or UVB radiation.

Finally, the subject of the present invention is the use of a true solution comprising at least one compound (a) dissolved in a solvent (b), said compound (a) being a chroman or chromene derivative corresponding to general formula (I) as defined above and said solvent (b) being chosen from the group consisting of polyethylene glycols, polypropylene glycols, derivatives thereof, ethoxylated fatty alcohols and polyols, and mixtures thereof, for the preparation of compositions intended for an external topical use.

The following examples are given without limitation and illustrate the present invention.

EXEMPLARY EMBODIMENT OF THE INVENTION

Procedure: A quantity of flavonoid (a) used in powdered form is accurately weighed in a 250 ml beaker. A precise quantity of excipient (b) is then added. The mixture is then vigorously stirred (mechanical stirring) at room temperature for 30 minutes. The solution is then heated to 50° C. so as to be clarified by simply passing through a Büchner filter. The true solution thus formed is then incorporated into the composition.

Examples of Cosmetic Formulations

Example 1

Genistein in PEG 300

|  | % by weight |
| --- | --- |
| Water | QS 100 |
| Squalane | 7.0 |
| Petrolatum | 3.0 |
| Glycerin | 3.0 |
| Isodecyl neopentanoate | 3.0 |
| Pentaerythrityl tetraethylhexanoate | 3.0 |
| Cyclomethicone | 2.0 |
| Cetearyl alcohol | 2.0 |
| Myristyl myristate | 1.0 |
| Laureth-23 | 1.0 |
| Beeswax | 1.0 |
| Sclerotium gum | 1.0 |
| Cetearyl glucoside | 0.6 |
| Cetyl palmitate | 0.1 |
| Cocoglycerides | 0.1 |
| PEG-300 | 4.0 |
| Genistein | 0.4 |

Preservatives QS

Example 2

Genistein in PEG 300

|  | % by weight |
| --- | --- |
| Water | QS 100 |
| Squalane | 7.0 |
| Petrolatum | 3.0 |
| Glycerin | 3.0 |
| Isodecyl neopentanoate | 3.0 |
| Pentaerythrityl tetraethylhexanoate | 3.0 |
| Cyclomethicone | 2.0 |
| Cetearyl alcohol | 2.0 |
| Myristyl myristate | 1.0 |
| Laureth-23 | 1.0 |
| Beeswax | 1.0 |
| Sclerotium gum | 1.0 |
| Cetearyl glucoside | 0.6 |
| Cetyl palmitate | 0.1 |
| Cocoglycerides | 0.1 |
| PEG-300 | 1.8 |
| Genistein | 0.2 |
| Preservatives | QS |

Example 3

Genistein in Liponic EG1

| | % by weight |
|---|---|
| Water | QS 100 |
| Squalane | 7.0 |
| Petrolatum | 3.0 |
| Glycerin | 3.0 |
| Isodecyl neopentanoate | 3.0 |
| Pentaerythrityl tetraethylhexanoate | 3.0 |
| Cyclomethicone | 2.0 |
| Cetearyl alcohol | 2.0 |
| Myristyl myristate | 1.0 |
| Laureth-23 | 1.0 |
| Beeswax | 1.0 |
| Sclerotium gum | 1.0 |
| Cetearyl glucoside | 0.6 |
| Cetyl palmitate | 0.1 |
| Cocoglycerides | 0.1 |
| Liponic EG1 | 4.0 |
| Genistein | 0.3 |
| Preservatives | QS |

Example 4

Genistein in Laureth-11

| | % by weight |
|---|---|
| Water | QS 100 |
| Squalane | 7.0 |
| Petrolatum | 3.0 |
| Glycerin | 3.0 |
| Isodecyl neopentanoate | 3.0 |
| Pentaerythrityl tetraethylhexanoate | 3.0 |
| Cyclomethicone | 2.0 |
| Cetearyl alcohol | 2.0 |
| Myristyl myristate | 1.0 |
| Laureth-23 | 1.0 |
| Beeswax | 1.0 |
| Sclerotium gum | 1.0 |
| Cetearyl glucoside | 0.6 |
| Cetyl palmitate | 0.1 |
| Cocoglycerides | 0.1 |
| Laureth-11 | 1.8 |
| Genistein | 0.2 |
| Preservatives | QS |

Tests of Solubility of Genistein in Polyethylene Glycols or Their Ethoxylated Homologs Procedure:

The genistein used in the solubility tests is a product of plant origin having a titer of 85 to 90% by weight. The quantity of genistein used in powdered form is accurately weighed in a 250 ml beaker. A precise quantity of excipient is then added. The mixture is then vigorously stirred (mechanical stirring) at room temperature for 30 minutes. The product is then directly assayed according to the protocol described below.

Assay Protocol:

The assay of genistein is carried out by reverse phase high-performance liquid chromatography (C18 stationary phase—acetic acid/acetonitrile mobile phase) and detection by UV spectrophotometry (absorption maximum of the compound). The external calibration uses a 99% pure reference substance.

This technique was validated from the point of view of its specificity (in relation to genistein and other flavones, but also in relation to the diluting PEGs used), its repeatability and its linearity (from 80% to 120% of the theoretical value).

Results:

Table 1 assembles various tests of solubility of genistein in polyethylene glycols (PEGs) or their ethoxylated homologs. The quantity of genistein assayed compared with the quantity of genistein used in the solvent makes it possible to conclude to the solubility of genistein in this solvent.

TABLE 1

| Excipient | Type | Genistein used (% by weight in the solution) | Genistein assayed (% by weight in the solution) | Solubility |
|---|---|---|---|---|
| PEG 200 | Polyethylene glycol | 12.0 | 10.9 | high |
| PEG 300 | Polyethylene glycol | 12.0 | 11.2 | high |
| PEG 400 | Polyethylene glycol | 12.0 | 10.1 | high |
| PEG 600 | Polyethylene glycol | 12.0 | 10.7 | high |
| PEG400 dilaurate | Fatty diester of PEG | 12.0 | 9.5 | high |
| Laureth 11 | Oxyethylenated C12 alcohol | 12.0 | 9.5 | high |
| Liponic EG1 | Ethoxylated glycerol | 10.0 | 9.1 | high |

The PEGs and their homologs, such as ethoxylated polyols, the esters of PEGs or the ethoxylated fatty alcohols are therefore good solvents for genistein. Also, the lower their molecular weight, the more marked the solvent power of the PEGs since higher solubilities are observed in the presence of PEGs 200 and 300. A maximum solubility is however observed in the presence of PEGs 300.

Table 2, which assembles tests of solubility of genistein at various concentrations in PEG 300, corroborates this result.

TABLE 2

| Excipient | Type | Genistein used (% by weight in the solution) | Genistein assayed (% by weight in the solution) | Solubility |
|---|---|---|---|---|
| PEG 300 | Polyethylene glycol | 8.0 | 7.6 | high |
| PEG 300 | Polyethylene glycol | 10.0 | 9.3 | high |
| PEG 300 | Polyethylene glycol | 12.0 | 11.2 | high |

Genistein can therefore be incorporated, in soluble form, into PEG 300 at a concentration close to 12% by weight relative to the total weight of the solution.

Influence of the Solubilization and of the Genistein Dose on the Reduction of Actinic Erythema

1—PROTOCOL

The reduction of actinic erythema induced by UVA+B irradiation with the compositions according to the present invention was demonstrated in healthy volunteers with the aid of a double blind test with a placebo. The placebo (P1) and the active products (P2), (P3) and (P4) were thus used to carry out this test.

The active ingredient, the galenic form and the solubilization of these various products are presented in the following table:

TABLE 3

| Reference test | Product | Final % of genistein in the cream | Galenic form | Solubilization |
|---|---|---|---|---|
| GE 100 Batch 135-05-0 G (P1) | Excipient | — | — | — |
| GE 100 Batch 135-05-0 A (P2) | Genistein 85% | 1.2 | Dispersed powder | low |
| GE 100 Batch 135-05-0 B (P3) | Genistein 85% | 1.2 | Solution containing 12% genistein in PEG 300 | high |
| GE 100 Batch 135-05-0 D (P4) | Genistein 85% | 0.6 | Solution containing 12% genistein in PEG 300 | high |

Several steps were followed:
Preliminary step: Evaluation of the individual Minimum Erythemal Dose ($MED_i$).
First step: Application of products P1 to P4 to a 35 cm² surface. The quantity applied is exactly 4 mg/cm². The zones for applying the products are modified by rotation from one volunteer to another.
Second step: Irradiation of the treated zones and of one untreated zone (control zone) fifteen minutes after application of the products, by positioning the $MED_i$ at the third hole.
Third steps: Visual readings of the erythema 6 and 24 hours after the irradiation.

a.) Choice of the Subjects 10 subjects per paired study are chosen from a panel of volunteers where they are selected according to the following inclusion criteria:
  brown, chocolate, blond or reddish-brown hair
  presence or absence of freckles
  age between 20 and 50 years
  sex unimportant
  absence of abnormal reaction to light b.) Irradiations The actinic erythema is triggered by irradiations carried out with a 150 watt xenon source equipped with a dichroic filter (reduction of the IR radiation) and a Schott WG 320 filter, having a thickness of 1 mm. This corresponds to a midday sun, on 21 June, at latitude 35° North.

The irradiations are performed on 6 zones (circular, diameter: 0.8 cm) arranged in rows, receiving doses in the form of a geometric progression (×1.25).

Beforehand, with the same apparatus, the individual MED of each subject was determined on the top of the back. Each of the experimental rows receives 0.64-0.8-1-1.25-1.56-1.95 MED.

The irradiations are performed symmetrically on either side of the vertebral column.

The irradiation times for the treated zones and for the untreated zone are determined so as to place the $MED_i$ at the third hole.

c.) Dosimetry

The administered UV doses are calculated with the aid of a calibrated ROBERTSON-BERGER dosimeter equipped with a UVB reading head. The results are expressed directly as values read on the dosimeter and expressed as MED (1 MED=25 mJ/cm²).

d.) Observations

The visual observations of the actinic erythemas are carried out at the 6th hour and at the 24th hour. The erythemas are evaluated according to the international classification of T (traces) at +++, noting the possible presence of an edema.

A numerical quantification corresponding to the degree of erythema is performed according to the following table:

TABLE 4

| Codification of the reading | Codification of the results |
|---|---|
| 0 | 0 |
| T | 1 |
| ± | 2 |
| +⁻ | 3 |
| + | 4 |
| +⁺ | 5 |
| ++⁻ | 6 |
| ++ | 7 |
| ++⁺ | 8 |
| +++ | 9 |

2—RESULTS

The results of the visual erythema reduction for the products P1, P2, P3 and P4, 6 and 24 hours after irradiation at the dose 1 MED are given in Table 5. The reduction of actinic erythema is expressed as a percentage.

TABLE 5

|  | P1 | P2 | P3 | P4 |
|---|---|---|---|---|
| 6 hours | 24.32% | 40.54% | 81.08% | 75.68% |
| 24 hours | 10.00% | 32.50% | 77.50% | 67.50% |

The results of the visual erythemal reduction for the products P1, P2, P3, P4, 6 and 24 hours after irradiation at the dose 1.56×MED are given in the following table:

TABLE 6

|  | P1 | P2 | P3 | P4 |
|---|---|---|---|---|
| 6 hours | 11.32% | 22.64% | 66.04% | 45.28% |
| 24 hours | 3.17% | 15.87% | 71.43% | 46.03% |

The details of the visual evaluation of the actinic erythemas on an untreated skin and on a treated skin, for various significant doses, at 1 MED and at 1.56 MED, are given in Tables 7 and 8, respectively:

TABLE 7

Visual readings of the erythemas 6 hours and 24 hours after irradiation, for the products P1 to P4 for the dose 1MED

|  | No. | CODE | MED | P1 | P2 | P3 | P4 | CONTROL |
|---|---|---|---|---|---|---|---|---|
| 6 hours | 1 | G004 | 1.95 | 2 | 1 | 0 | 1 | 4 |
| 6 hours | 2 | A121 | 1.56 | 1 | 1 | 1 | 1 | 1 |
| 6 hours | 3 | B002 | 3.05 | 4 | 2 | 1 | 1 | 4 |
| 6 hours | 4 | A117 | 2.44 | 3 | 3 | 1 | 1 | 4 |
| 6 hours | 5 | F067 | 2.44 | 2 | 4 | 1 | 1 | 4 |
| 6 hours | 6 | K014 | 1.95 | 4 | 2 | 1 | 1 | 4 |
| 6 hours | 7 | I087 | 1.56 | 1 | 1 | 0 | 0 | 4 |
| 6 hours | 8 | L017 | 2.44 | 2 | 2 | 0 | 1 | 4 |
| 6 hours | 9 | G026 | 1.56 | 4 | 4 | 1 | 1 | 4 |
| 6 hours | 10 | H117 | 1.95 | 5 | 2 | 1 | 1 | 4 |
| 24 hours | 1 | G004 | 1.95 | 4 | 3 | 0 | 1 | 4 |
| 24 hours | 2 | A121 | 1.56 | 4 | 4 | 1 | 2 | 4 |
| 24 hours | 3 | B002 | 3.05 | 4 | 3 | 1 | 2 | 4 |
| 24 hours | 4 | A117 | 2.44 | 2 | 2 | 1 | 1 | 4 |
| 24 hours | 5 | F067 | 2.44 | 3 | 2 | 1 | 1 | 4 |
| 24 hours | 6 | K014 | 1.95 | 4 | 2 | 1 | 1 | 4 |
| 24 hours | 7 | I087 | 1.56 | 3 | 3 | 1 | 1 | 4 |
| 24 hours | 8 | L017 | 2.44 | 4 | 3 | 1 | 2 | 4 |
| 24 hours | 9 | G026 | 1.56 | 4 | 3 | 1 | 1 | 4 |
| 24 hours | 10 | H117 | 1.95 | 4 | 2 | 1 | 1 | 4 |
| Mean 6 h |  |  | 2.09 | 2.80 | 2.20 | 0.70 | 0.90 | 3.70 |
| Student/T 6 h |  |  |  | 0.054 | 0.003 | 0.000 | 0.000 |  |
| Reduction/T |  |  |  | 24.32% | 40.54% | 81.08% | 75.68% |  |
| Student/P1 6h |  |  |  |  | 0.217 | 0.000 | 0.001 |  |
| Reduction/P1 |  |  |  |  | 21.43% | 75.00% | 67.86% |  |
| Mean 24 h |  |  | 2.09 | 3.60 | 2.70 | 0.90 | 1.30 | 4.00 |
| Student/T 24 h |  |  |  | 0.104 | 0.000 | 0.000 | 0.000 |  |
| Reduction/T |  |  |  | 10.00% | 32.50% | 77.50% | 67.50% |  |
| Student/P1 24 h |  |  |  |  | 0.004 | 0.000 | 0.000 |  |
| Reduction/P1 |  |  |  |  | 25.00% | 75.00% | 63.89% |  |
| Mean |  |  | 2.09 | 3.20 | 2.45 | 0.80 | 1.10 | 3.85 |
| Student/T |  |  |  | 0.012 | 0.000 | 0.000 | 0.000 |  |
| Reduction/T |  |  |  | 16.88% | 36.36% | 79.22% | 71.43% |  |
| Student/P1 |  |  |  |  | 0.007 | 0.000 | 0.000 |  |
| Reduction/P1 |  |  |  |  | 23.44% | 75.00% | 65.63% |  |

TABLE 8

Visual readings of the erythemas 6 hours and 24 hours after irradiation, for the products P1 to P4 for the dose 1.56 × MED

|  | No. | CODE | MED | P1 | P2 | P3 | P4 | CONTROL |
|---|---|---|---|---|---|---|---|---|
| 6 hours | 1 | G004 | 1.95 | 5 | 4 | 0 | 4 | 7 |
| 6 hours | 2 | A121 | 1.56 | 1 | 1 | 1 | 1 | 1 |
| 6 hours | 3 | B002 | 3.05 | 7 | 5 | 4 | 4 | 7 |
| 6 hours | 4 | A117 | 2.44 | 5 | 5 | 3 | 4 | 5 |
| 6 hours | 5 | F067 | 2.44 | 5 | 5 | 4 | 4 | 7 |
| 6 hours | 6 | K014 | 1.95 | 4 | 2 | 1 | 1 | 4 |
| 6 hours | 7 | I087 | 1.56 | 5 | 5 | 1 | 4 | 5 |
| 6 hours | 8 | L017 | 2.44 | 5 | 5 | 2 | 4 | 7 |
| 6 hours | 9 | G026 | 1.56 | 5 | 5 | 1 | 1 | 5 |
| 6 hours | 10 | H117 | 1.95 | 5 | 4 | 1 | 2 | 5 |
| 24 hours | 1 | G004 | 1.95 | 7 | 7 | 1 | 4 | 7 |
| 24 hours | 2 | A121 | 1.56 | 5 | 5 | 1 | 3 | 5 |
| 24 hours | 3 | B002 | 3.05 | 8 | 5 | 4 | 5 | 8 |
| 24 hours | 4 | A117 | 2.44 | 5 | 5 | 1 | 4 | 7 |
| 24 hours | 5 | F067 | 2.44 | 7 | 5 | 3 | 4 | 7 |
| 24 hours | 6 | K014 | 1.95 | 5 | 4 | 2 | 1 | 5 |
| 24 hours | 7 | I087 | 1.56 | 7 | 7 | 2 | 4 | 7 |
| 24 hours | 8 | L017 | 2.44 | 5 | 4 | 2 | 4 | 5 |
| 24 hours | 9 | G026 | 1.56 | 7 | 7 | 1 | 1 | 7 |
| 24 hours | 10 | H117 | 1.95 | 5 | 4 | 1 | 4 | 5 |
| Mean 6 h |  |  | 2.09 | 4.70 | 4.10 | 1.80 | 2.90 | 5.30 |
| Student/T 6 h |  |  |  | 0.081 | 0.009 | 0.000 | 0.000 |  |
| Reduction/T |  |  |  | 11.32% | 22.64% | 66.04% | 45.28% |  |
| Student/P1 6 h |  |  |  |  | 0.051 | 0.000 | 0.002 |  |
| Reduction/P1 |  |  |  |  | 12.77% | 61.70% | 38.30% |  |
| Mean 24 h |  |  | 2.09 | 6.10 | 5.30 | 1.80 | 3.40 | 6.30 |

TABLE 8-continued

Visual readings of the erythemas 6 hours and
24 hours after irradiation, for the products P1 to P4
for the dose 1.56 × MED

| | No. | CODE | MED | P1 | P2 | P3 | P4 | CONTROL |
|---|---|---|---|---|---|---|---|---|
| Student/T 24 h | | | | 0.343 | 0.015 | 0.000 | 0.000 | |
| Reduction/T | | | | 3.17% | 15.87% | 71.43% | 46.03% | |
| Student/P1 24 h | | | | | 0.037 | 0.000 | 0.000 | |
| Reduction/ P1 | | | | | 13.11% | 70.49% | 44.26% | |
| Mean | | | 2.09 | 5.40 | 4.70 | 1.80 | 3.15 | 5.80 |
| Student/T | | | | 0.042 | 0.000 | 0.000 | 0.000 | |
| Reduction/T | | | | 6.90% | 18.97% | 68.97% | 45.69% | |
| Student /P1 | | | | | 0.003 | 0.000 | 0.000 | |
| Reduction/P1 | | | | | 12.96% | 66.67% | 41.67% | |

3—INTERPRETATION OF THE RESULTS

Relationship Between P1 (Placebo) and T (Untreated Control Skin):

According to the results of the visual reading, it is observed that 6 hours and 24 hours after irradiation of the treated and untreated zones, the results are not significant for the excipient P1 (student $p>0.05$). However, when the results at 6 hours and at 24 hours are combined, and therefore the number of observations increased (20), it is observed that the results are significant (student $p<0.05$). It can therefore be asserted that the excipient contains active agents which allow a slight erythemal reduction.

A comparison was subsequently carried out of the products studied P2 to P4, compared with the excipient P1 and with the control T.

Significance of the Results on Comparing the Products P1 to P4 with the Untreated Control Skin (Student Test):

Product P1

For the product P1, the results are not significant at the doses 1 MED and 1.56×MED, 6 hours and 24 hours after irradiation (student $p>0.05$).

Products P2 to P4

For the products P2 to P4, it is observed that 6 hours and 24 hours after irradiation, at the doses 1 MED and 1.56×MED, the results are significant (student $p<0.05$).

Significance of the Results on Comparing the Products P2 to P4 with the Excipient P1 (Student's Test):

Product P2

For the product P2, it is observed that, at the doses of 1 MED and 1.56×MED, the results are not significant 6 hours after irradiation of the treated and untreated zones (student $p>0.05$). The results are however significant for the two doses, 24 hours after irradiation and when the results at 6 and at 24 hours are totaled (student $p<0.05$).

Products P3 and P4

For the products P3 and P4, it is observed that at the doses of 1 MED and 1.56×MED, the results are significant 6 hours and 24 hours after irradiation (student $p<0.05$).

Decreasing Classification of the Products P2 to P4 Compared with the Visual Rythemal Reduction at the Dos 1 MED
24 hours after irradiation: P3-P4-P2
By combining the results for the observations at 6 hours and at 24 hours after irradiation: P3-P4-P2

4—CONCLUSIONS

Two major conclusions can be drawn as regards this study:
The solubilization of genistein is an essential factor in its antierythemal activity. Indeed, the antierythemal activity of genistein is increased when the latter is solubilized beforehand in PEG 300.
The antierythemal activity of genistein is dependent on the dose used. Indeed, the product P3 (1.2% genistein) is more effective than the product P4 (0.6% genistein) 6 and 24 hours after irradiation.

The invention claimed is:

1. A composition intended for an external topical use comprising at least one true solution consisting of at least one compound (a) and a solvent (b), wherein said compound (a) is dissolved in said solvent (b) and said solvent (b) is chosen from polyethylene glycols having a molecular weight ranging from 200 to 300, and mixtures thereof, and wherein said at least one compound (a) is genistein.

2. The composition of claim 1, wherein said solvent (b) is polyethylene glycol 300.

3. The composition of claim 1, wherein said at least one compound (a) is present at a concentration ranging from 0.1 to 1.2% by weight relative to the total weight of the composition.

4. The composition of claim 1, wherein said at least one compound (a) is present at a concentration ranging from 0.1 to 12% by weight relative to the total weight of said true solution.

5. A method for preparing a composition of claim 1, comprising solubilizing said at least one compound (a) in said solvent (b), at room temperature, with stirring, for a period ranging from 10 to 120 minutes.

6. The method of claim 5, wherein said period is 30 minutes.

7. A method for protecting the skin against sun, comprising the administration to a subject of the composition of claim 1.

8. The method of claim 7, wherein said composition is an antioxidant, anti-free-radical agent, anti-inflammatory agent or a vasculotropic agent.

9. The method of claim 7, wherein said composition is a medicament or a cosmetic composition.

10. A method for reducing erythemas, comprising the administration to a subject of the composition of claim 1.

11. The method of claim 10, wherein said erythemas are actinic erythemas induced by UVA and/or UVB radiation.

12. The method of claim 10, wherein said composition is a medicament or a cosmetic composition.

13. A method for the external topical administration of a composition comprising a true solution consisting of at least one compound (a) dissolved in a solvent (b), wherein said at least one compound (a) is genistein and wherein said solvent (b) is chosen from polyethylene glycols having a molecular weight ranging from 200 to 300, and mixtures thereof.

* * * * *